(12) United States Patent
Liang et al.

(10) Patent No.: US 10,525,113 B2
(45) Date of Patent: Jan. 7, 2020

(54) MICELLAR POLYPEPTIDE VACCINE HAVING PEGYLATED PHOSPHOLIPIDS AS CARRIER

(71) Applicant: INSTITUTE OF BIOPHYSICS, CHINESE ACADEMY OF SCIENCES, Beijing (CN)

(72) Inventors: Wei Liang, Beijing (CN); Yan Qin, Beijing (CN)

(73) Assignee: SHANGHAI TIANHUI CHEMICAL PHARMACEUTICAL CO. LTD, Shanghai (CN)

(*) Notice: Subject to any disclaimer, the term of this patent is extended or adjusted under 35 U.S.C. 154(b) by 103 days.

(21) Appl. No.: 15/520,426

(22) PCT Filed: Oct. 19, 2015

(86) PCT No.: PCT/CN2015/092192
§ 371 (c)(1),
(2) Date: Apr. 20, 2017

(87) PCT Pub. No.: WO2016/062227
PCT Pub. Date: Apr. 28, 2016

(65) Prior Publication Data
US 2017/0312352 A1    Nov. 2, 2017

(30) Foreign Application Priority Data
Oct. 22, 2014    (CN) .......................... 2014 1 0570624

(51) Int. Cl.
| | | |
|---|---|---|
| A61K 33/24 | (2019.01) | |
| A61K 39/00 | (2006.01) | |
| A61K 9/107 | (2006.01) | |
| A61K 39/395 | (2006.01) | |

(52) U.S. Cl.
CPC ........ *A61K 39/0011* (2013.01); *A61K 9/1075* (2013.01); *A61K 33/24* (2013.01); *A61K 39/39558* (2013.01); *A61K 2039/505* (2013.01); *A61K 2039/54* (2013.01); *A61K 2039/55572* (2013.01); *A61K 2039/57* (2013.01); *A61K 2039/572* (2013.01); *A61K 2039/585* (2013.01)

(58) Field of Classification Search
CPC .......................... A61K 39/0011; A61K 33/24
USPC ....................................................... 424/155.1
See application file for complete search history.

(56) References Cited

U.S. PATENT DOCUMENTS

2011/0251269 A1* 10/2011 Seo .................. A61K 9/0019
514/449

FOREIGN PATENT DOCUMENTS

| CN | 1840193 A | 10/2006 |
|---|---|---|
| CN | 103784400 A | 5/2014 |

OTHER PUBLICATIONS

Wang et al (Mol Pharm, 2010, 7(4): 1007-1014).*
Chen et al (Cancer Epidemiology, 2013, 37: 172-178).*
Nishiyama et al (Cancer Research, 2003, 63: 8977-8983).*
Wang et al (Gynecol Oncol, 2010, 119(3): 564-570).*
Bershteyn et al (J Control Release, 2012, 157(3): 1-27).*
Torchilin (Pharm Res, 2007, 24: 1-16).*
Torchilin et al (Cell Mol Life Sci, 2004, 61: 2549-2559).*
Arlen PM, et al. A randomized phase II study of docetaxel alone or in combination with PANVAC-V (vaccinia) and PANVAC-F (fowlpox) in patients with metastatic breast cancer (NCI 05-C-0229). Clin Breast Cancer. 2006, pp. 176-179, vol. 7.
Gulley JL, et al. Immunologic and prognostic factors associated with overall survival employing a poxviral-based PSA vaccine in metastatic castrate-resistant prostate cancer. Cancer Immunol Immunother. 2009.
Huang X, Yang Y. Innate Immune Recognition of Viruses and Viral Vectors. Hum Gene Ther. 2009, pp. 293-301, vol. 20.
Hailemichael Y, et al. Persistent antigen at vaccination sites induces tumor-specific CD8+ T cell sequestration, dysfunction and deletion. Nat Med. 2013;19(4):pp. 465-472.
Minato, S. et al, "Application of polyethyleneglycol (PEG)-modified liposomes for oral vaccine: effect of lipid dose on systemic and mucosal immunity", Journal of Controlled Release. vol. 89, No. 2, Apr. 30, 2003(Apr. 30, 2003), pp. 189-197, see the whole document, particularly p. 190, right column.
Zhuang, Y. et al. "PEGylated cationic liposomes robustly augment vaccine-induced immune responses:Role of lymphatic trafficking and biodistribution". Journal of Controlled Release. vol. 159, No. 1, Apr. 30, 2012(Apr. 30, 2012), pp. 135-142, see the whole document, particularly abstract.
Wichit, A, et al. "Polymeric Micelles of PEG-PE as Carriers of All-Trans Retinoic Acid for Stability improvement". AAPS PHARMSCITECH. vol. 13, No. 1, Mar. 31, 2012(Mar. 31, 2012), pp. 336-343, see the whole document, particularly abstract, and p. 336, right column.

(Continued)

*Primary Examiner* — Sean E Aeder
(74) *Attorney, Agent, or Firm* — Gokalp Bayramoglu

(57) ABSTRACT

Disclosed in the present invention is micellar polypeptide vaccine having pegylated phospholipid as carrier. The vaccine can prevent or treat tumors or can be used as combination formulation with anti-cancer activity formulation. The micellar polypeptide vaccine is formed of self-assembling pegylated phospholipid (PEG-PE) and antigenic polypeptides, the pegylated phospholipid being compound formed of polyethylene glycol (hydrophilic blocks) covalently bonded to nitrogenous bases on phospholipid molecule (hydrophobic blocks). The particle diameter of the micellar vaccine is 10-100 nm, and the antigenic polypeptides carried therein are polypeptides of 5-100 amino acids. The micellar polypeptide vaccine may also contain immunoadjuvant.

2 Claims, 11 Drawing Sheets

(56) References Cited

OTHER PUBLICATIONS

Black, Matthe\n, Thesis(Ph.D.)—University of California, Dec. 31, 2011, abstract.
Young Tag Ko et al. Self-assembling micelle-like nanoparticles based on phospholipid-polyethyleneimine conjugates for systemic gene delivery,Journal of Controlled Release, Oct. 7, 2008, pp. 132-138, vol. 133.

* cited by examiner

MICELLAR POLYPEPTIDE VACCINE HAVING PEGYLATED PHOSPHOLIPIDS AS CARRIER

CROSS REFERENCE

This application is the national phase of International Application No. PCT/CN2015/092192, filed on Oct. 19, 2015, which is based upon and claims priority to Chinese Patent Application CN201410570624.7, filed on Oct. 22, 2014, the entire contents of which are incorporated herein by reference.

TECHNICAL FIELD

The present invention relates to the field of medical biotechnology, more particularly, to micellar polypeptide vaccine having pegylated phospholipid as a carrier and a preparation method and application thereof.

BACKGROUND

A tumor therapeutic vaccine designed by using nanoscale materials as the carrier is a new way to treat the tumor. Existing researches show that using the nanoscale material to carry protein antigen can increase the imnmnogenicity of the antigen. This phenomenon may relate to the relatively huge surface area and the complex structure of the nanoscale material. Meanwhile, the nanoscale material carrier can protect the protein antigen to a certain extent to prevent the protein antigen from degradation by the protease and the inner-system quickly, helping the protein antigen play its role effectively. Additionally, the nanoscale material carrier carrying the protein antigen is easy for intake and process by antigen present cells (APCs), especially dendritic cells (DCs) to make the DCs process and present a large amount of protein antigen to induce a more effective immune response. Using specific nanoscale material to entrap tumor-specific antigen and immunoadjuvant to form tumor therapeutic vaccine and inoculating the vaccine to a patient with tumor can stimulate the immune system of the patient, trigger an immune response to kill tumor cells, and reduce or eliminate the remains of tumor focuses in the body after operation or radiotherapy and chemotherapy.

Currently, although many kinds of tumor vaccine design schemes, using nanoscale materials as a carrier, have appeared, but these all face critical technical obstacles. Although the tumor vaccine using a virus, virus-like particle or virosome as a carrier (1. Arlen P M, et al. A randomized phase II study of docetaxel alone or in combination with PANVAC-V (vaccinia) and PANVAC-F (fowlpox) in patients with metastatic breast cancer (NCI 05-C-0229). Clin Breast Cancer. 2006; 7:176-179; 2. Gulley J L, et al. Immunologic and prognostic factors associated with overall survival employing poxviral-based PSA vaccine in metastatic castrate-resistant prostate cancer. Cancer Immunol Immunother. 2009) can stimulate the organism to induce an immune response at the beginning of use, the protein component of the virus itself is an effective antigen and dominates. As a result, the induced immune response is mainly aiming at the antigen of the virus carrier itself rather than the tumor specific antigen carried by the virus carrier. This effect is more obvious, especially in the situation where the antigenicity of the tumor specific antigen is relatively weak. In order to improve the immunotherapy effect of the therapeutic vaccine, normally multiple immunizations will be conducted. In this situation, the immune response (mainly the antibody response) to the virus carrier itself, induced by the previous immunization, will significantly reduce the effect of the subsequent immunotherapy. Moreover, the vaccine designed by using common virus (for example, adenovirus, poxvirus, etc.) as carrier normally has a significantly reduced immunotherapy effect due to the possible immune protection generated by the patient's early virus infection (Huang X, Yang Y. Innate immune recognition of viruses and viral vectors. Hum Gene Ther. 2009; 20:293-301.).

For nanovaccine using lipidosome as a carrier, since the carrier itself does not have immunogenicity, the immune effect of the tumor specific antigen can be improved. However, due to the size and component of the lipidosome carrier, its particle cannot effectively diffuse into the draining lymph node after the hypodermic vaccination. Some of the vaccine components remain in the vaccinating area for a long time. As a result, a large amount of tumor antigen-specific cytotoxic lymphocytes (CTLs), induced by immunization, will immigrate to the vaccinating area rather than the tumor growing area so that the specific immune response to the tumor is significantly lowered. (Hailemichael Y, et al. Persistent antigen at vaccination sites induces tumor-specific CD8+T cell sequestration, dysfunction, and deletion. Nat Med. 2013; 19(4): 465-72.) In addition, due to the characteristics of the preparation of lipidosome, the obtained product normally has poor homogeneity, large particle size range, and normal repeatability among production batches. Therefore, it exists a certain difficulty in quality control.

Micellar carrier is a kind of nanoparticles formed of self-assembling amphiphilic polymer molecules including both hydrophilic blocks and hydrophobic blocks. The assembly of the micellar nanoparticles is that the polymer molecules spontaneously form a thermodynamically stable system in an aqueous solution. This process is caused by free energy decrease due to spontaneous accumulation and polymerization of the hydrophobic blocks withdrawn from the aqueous solution. Comparing with surfactants with low molecular-weight, the critical micelle concentration (CMC) of the amphiphilic polymer is lower such that the polymer micelles can resist the dilution of the solution. Meanwhile, the micellar core formed of hydrophobic blocks has a compact structure which makes it hard to dissociate after being diluted with a large amount of body fluid. Therefore, it has a better stability. Generally, the hydrophilic blocks of the amphiphilic polymer molecule are made of polyethylene glycol (PEG), which has a good water solhbility and a high level of hydration characteristic such that it can provide sufficient steric hindrance for the micellar particle at the shell area thereof. Additionally, it has good biocompatibility and is a widely used pharmaceutic adjuvant verified by FDA. There are lots of materials that can be used for the hydrophobic blocks of the amphiphilic polymer molecule, and the material used is a key factor for the drug loading efficiency and stability of the micellar carrier. Based on the chemical structure, the lipophilic group of the hydrophobic blocks can be divided into three types, i.e., polyester derivative, poly-amino acid derivative, and pluronics types. In core blocks of the polyester type, poly-lactic acid (PLA), poly-caprolactone (PCL), and poly-glycolic acid are all materials confirmed by FDA with good biocompatibility. In core blocks of the poly-amino acid type, materials such as poly-aspartic acid (PAsp), polyglutamic acid (PGlu), poly-L-lysine (PLys), poly-histidine (Phis), and so on have been commonly used. The pluronics is the triblock copolymer of polyethylene oxide-polypropylene oxide-polyethylene oxide, and can be written as PEOm-PPOn-PEOm.

The pegylated phospholipid is a new type of amphiphilic polymer molecule. The hydrophilic blocks of the pegylated phospholipid are polyethylene glycols, and the hydrophobic blocks of the pegylated phospholipid are lipid molecules. The polyethylene glycol molecules are covalently bonded with nitrogenous bases of the lipid molecules. Currently, the pegylated phospholipid is used as an entrapping material to mainly entrap chemotherapeutic drugs having small molecules. The advantages are that: 1) the phospholipid with hydrophobic cores can entrap a poorly soluble drug to significantly improve the solubility of the drug; 2) the polyethylene glycol with hydrophilic shells can protect the drug molecules inside the micelle from being absorbed or degraded from outside to help the drug escape from intake by the reticuloendothelial system and extend the circulation time of the drug; 3) the releasing of the drug can be controlled and the intracorporal distribution of the drug can be optimized to obtain a better therapeutic effect (without causing immune response). However, there is few research about the entrapment of pegylated phospholipid micelle to protein or peptide, and no research about tumor therapeutic vaccine developed by using micelles made of the pegylated phospholipid as carrier system is reported in this country and abroad.

Monophosphoryl Lipid A (MPLA) is a common immunoadjuvant (see FIG. 9 for structure), which is a new type of immunoadjuvant obtained by chemically modifying lipopolysaccharide (LPS) derived from *salmonella* R595. Comparing with LPS, MPLA substantially keeps the ability of immune stimulation while significantly lowering the endotoxin toxicity. Thus, it becomes a safer and more effective immunoadjuvant, and has been granted by FDA as immunoadjuvant entering clinical. Similar to the molecular mechanism by which the LPS functions, MPLA functions by interacting with Toll-like receptor in 4 phases, activating the signal passage downstream of the MPLA that relates to natural immunization, activating natural immunization responses, promoting the expression of interferon γ and tumor necrosis factor α, while activating dendritic cells to further activate an acquired immune response.

SUMMARY OF THE INVENTION

The present invention relates to micellar polypeptide vaccine that can prevent and treat tumor.

The micellar polypeptide vaccine of the present invention is formed of self-assembling pegylated phospholipid (PEG-PE) and antigenic polypeptide. The pegylated phospholipid is a compound formed of polyethylene glycol (hydrophilic block) covalently bonded to nitrogenous base on phospholipid molecule (hydrophobic block).

The polyethylene glycol hydrophilic block of the pegylated phospholipid molecule is PEG molecule having molecular weight of 500 to 10000, preferably, PEG 1500-3000, most preferably. PEG 2000.

The particle diameter of the micellar vaccine of the present invention is 10-100 nm, preferably, 10-50 nm, most preferably, 20 nm.

The antigenic polypeptide of the present invention is polypeptide having a length of 5-100 amino acids, preferably, polypeptide of 10-50 amino acids, more preferably, polypeptide of 20-30 amino acids, most preferably, E7 polypeptide or OT-1 polypeptide.

The E7 antigenic polypeptide is tumor-associated antigen which roots in human type-16 papilloma virus (HPV16), with palmitic acid molecule connected to the N-terminal, i.e., E7-20 polypeptide; $E7_{43-62}$ sequence: palmitic acid-GQAEPDRAHYNIVTFCCKCD.

The OT-1 polypeptide of the present invention is polypeptide of 17 amino acids that is derived from OVA and includes the epitope of OVA protein in H-2 Kb typing mouse specific CTL: OVA257-264. The amino acid sequence structure is palmitic acid-EQLESIINFEKLTEWKD.

The micellar polypeptide vaccine of the present invention may also comprise immunoadjuvant for adjusting body immune function. The immunoadjuvant comprises Freund's adjuvant, aluminum hydroxide adjuvant. Toll-like receptor agonist (including but not limited to monophosphoryl lipid A adjuvant, Flagellin, Imidazoquinoline, Resiquimod, CpG, TLR7/8 agonist, and so on). Preferably, the immunoadjuvant is the monophosphoryl lipid A (MPLA) adjuvant.

In the micellar polypeptide vaccine of the present invention, the range of the molar ratio of the dosage of the pegylated phospholipid polymer molecule, the antigenic polypeptide and the immunoadjuvant is 720:4-160:3-80. Preferably, the molar ratio is 180:4:3.

The micellar polypeptide vaccine agent of the present invention is in a solution form or in a lyophilized form.

The preparation method of the micellar polypeptide vaccine of the present invention is:

(1) dissolving PEG-PE carrier molecules, antigenic polypeptide molecules, immunoadjuvant molecules in volatile organic solvent to prepare carrier molecule solution, antigenic polypeptide solution, and immunoadjuvant solution;

(2) evenly mixing the carrier molecule solution, the antigenic polypeptide solution, and the immunoadjuvant solution obtained in step (1) in a certain ratio;

(3) removing all the organic solutions obtained in step (2) to make the carrier molecules, the antigenic polypeptide molecules and the immunoadjuvant molecules form a mixed lipid membrane that is evenly distributed;

(4) dissolving the mixed lipid membrane obtained in step (3) in a certain amount of deionized water or saline, hydrating the lipid membrane evenly in an incubating condition, and then standing at room temperature for a certain time to obtain micellar vaccine solution;

(5) filtering and sterilizing the micellar vaccine solution obtained in step (4) with a 0.22 μm filter membrane:

(6) as required, adding a certain amount of lyophilized protective agent to the micellar vaccine solution obtained in step (5), and then lyophilizing the vaccine solution to prepare lyophilized micellar vaccine powder.

In step (1) of the preparation method of micellar polypeptide vaccine according to the present invention, the volatile organic solvent is methanol, chloroform, dichloromethane, ethyl acetate, ethyl alcohol, acetone, glacial acetic acid, and so on, or the mixture thereof.

In step (3) of the preparation method of micellar polypeptide vaccine according to the present invention, the method of removing the organic solutions is preferably decompressing water bath and heating rotary evaporation.

In step (4) of the preparation method of micellar polypeptide vaccine according to the present invention, the incubating condition preferably means incubating with water bath at 55-t for 30 minutes.

In step (6) of the preparation method of micellar polypeptide vaccine according to the present invention, the lyophilized protective agent is preferably selected from the group consisting of mannitol, lactose, dextran, and so on, the concentration of which is 0.05 g/ml.

The present invention also relates to the application of the micellar polypeptide vaccine agent to the drugs for treating tumors, including solid tumors and non-solid tumors. Particularly, the application refers to administering a certain dose of the micellar polypeptide vaccine agent to a patient via subcutaneous injection or intravenous injection.

The present invention also relates to the application of the micellar polypeptide vaccine agent in preventing tumors, including solid tumors and non-solid tumors. Particularly, the application relates to administering a certain dose of the micellar polypeptide vaccine agent to a patient via subcutaneous injection, intramuscular injection, submucous injection, or intravenous injection.

The present invention also relates to an anti-tumor vaccine product, which comprises the micellar polypeptide vaccine and pharmaceutically acceptable auxiliary materials.

The present invention also relates to the application of the micellar polypeptide vaccine in preparing drugs for treating or preventing tumors, including solid tumors and non-solid tumors.

The present invention also relates to a treatment method by using the micellar polypeptide vaccine in combination with other anti-tumor drugs. Particularly, the method includes using the micellar polypeptide vaccine in combination with other anti-tumor drugs, including chemotherapy drug, monoclonal antibody drug, cytokine drug, and chemokine drug.

The present invention shows a synergistic effect in treatment by using new micellar polypeptide vaccine in combination with one or more effective drugs in anti-tumor treatment such that the survival rate and the cure rate are significantly increased.

Based on this, the present invention provides a strategy of combined agent for combining administration of the micellar polypeptide vaccine and effective anti-cancer therapeutic drugs (including, but not limited to, alkylating agent, nucleotide analog, antimetabolite, anti-tumor antibiotics, topoisomerase I inhibitor, topoisomerase II inhibitor, antimitotic drug, platinum derivate drug, cytokine drug, monoclonal antibody drug) in anti-cancer treatment.

The micellar polypeptide vaccine of the present invention and other anti-cancer therapeutic drugs can be administered at the same time, separately, or sequentially. The specific plan needs to be determined according to experiment/clinical results. Therefore, the other object of the present invention is to use the combined agent of the micellar polypeptide vaccine and effective anti-cancer therapeutic drugs in anti-cancer treatment simultaneously, separately, or sequentially. For example, the micellar tumor therapeutic vaccine is administered after cisplatin treatment in embodiment 11, while the micellar tumor therapeutic vaccine is administered together with PD-L1 antigen in embodiment 12.

In a preferred embodiment, the anti-cancer therapeutic drug in the combined agent of the present invention is preferably platinum derivate, more preferably, cisplatin.

Preferably, the micellar polypeptide vaccine in the combined agent is micellar polypeptide vaccine comprising MPLA and HPV16 E7 antigenic polypeptide.

Most preferably, the combined agent is combined agent of micellar polypeptide vaccine comprising MPLA and HPV16 E7 antigenic polypeptide and using cisplatin as an anti-cancer therapeutic drug.

As above, the combined agent according to the present invention can be used to treat cancer. In the most preferred embodiment, the combined agent of the present invention is used to treat cervical cancer caused by HPV16 infection.

The component of the combined agent according to the present invention can be administered in any medically acceptable manners. These manners include oral administration, parenteral administration, or zone therapy, such as implantation. The oral administration includes administering the component of the combined agent in a proper oral form, including troche, capsule, suspension, emulsion, powder, syrup, and the like. The parenteral administration includes administering the component of the combined agent via subcutaneous injection, intravenous injection, or intramuscular injection.

Injection is a preferred administration approach in which the administration time and the level of dose can be maximally controlled.

The preferred method and order for administering the combined agent can vary according to the specific pharmaceutic preparation, specific cancer, the severity of the specific disease to be treated, and the particular situation of the patient subjected to the treatment. The range of dosage of administration of the combined agent according to the present invention can be determined by those skilled in the art according to the particular situation of the patient. Therefore, the dosage schedule can be used to any regular treatments, according to the specific patient situation, reaction, and related treatment, and needs adjustment according to the change of the illness state and (or) other clinical situations.

In the most preferred combined agent of the present invention for treating cervical cancer, the technology for preparing pharmaceutically acceptable carriers or excipients are known in the art. For example, the excipients generally may comprise, for example, pharmaceutically acceptable salts, buffers, preservatives and (or) compatible carriers, or combinations thereof. The pharmaceutically acceptable carriers mean one or more compatible solid or liquid fillers, diluents or capsules that are suitable for administration of manuals including human beings.

The combination of drugs suitable for parenteral administration is formulated as sterile, and the sterile composition may be a sterile solution or suspension dissolved in a non-toxic diluent or solvent which can be accepted by gastrointestinal tract. The amount of the active ingredient in the combined agent may vary widely depending on factors such as the route of administration and excipients.

For example, the dosage of the tumor treating micellar polypeptide vaccine that the combined agent may comprise is 250 µg to 2.5 mg, and 1 mg to 1000 mg of platinum-based derivatives, such as cisplatin.

Another aspect of the present invention is to provide a method of treating mammal (including human being) with cancer. The method comprises administering to said mammal combined agent comprising micellar polypeptide as described above and an effective dose of at least one drug that can provide a synergistic anti-cancer effect. The at least one drug is selected from the group consisting of alkylating agents (cyclophosphamide, carmustine, etc.), nucleotide analogues (methotrexate, fluorouracil, etc.), antimetabolites (hydroxyurea, UFT, etc.), anti-tumor antibiotics (doxorubicin, mitomycin, etc.), topoisomerase I inhibitors (hydroxycamptothecin, topotecan, etc.), topoisomerase II inhibitors (etoposide, teniposide), antimitotic drugs (paclitaxel, vinorelbine, etc.), platinum derivatives (cisplatin, carboplatin, etc.), cytokine drugs (IL-2, IFNγ, etc.), monoclonal antibody (Her2 monoclonal antibody, PD-L1 monoclonal antibody, etc.) and so on.

The present invention particularly provides a treating method for treating cervical cancer.

As used herein, the term "synergistic anti-cancer effect" refers to administering combined agent comprising an effective dose of the above tumor-treating micelle polypeptide vaccine and an effective amount of at least another drug that can provide a synergistic anti-cancer effect in mammals, including human beings, in order to achieve the effect of control the growth of the tumor, shrink the tumor, or extinct the tumor. The at least one drug is selected from the group consisting of alkylating agents (cyclophosphamide, carmustine, etc.), nucleotide analogues (methotrexate, fluorouracil, etc.), antimetabolites (hydroxyurea, UFT, etc.), anti-tumor antibiotics (doxorubicin, mitomycin, etc.), topoisomerase I inhibitors (hydroxycamptothecin, topotecan, etc.), topoisomerase II inhibitors (etoposide, teniposide), antimitotic drugs (paclitaxel, vinorelbine, etc.), platinum derivatives (cisplatin, carboplatin, etc.), cytokine drugs (IL-2, IFNγ, etc.), monoclonal antibody (Her2 monoclonal antibody, PD-L monoclonal antibody, etc.) and so on.

As used herein, the term "administering" or "administration" refers to parenteral and/or oral and/or localized administration as defined above.

In the method of the present invention, the tumor-treating micellar polypeptide vaccine may be mixed with at least one other anti-cancer drug selected from the group consisting of alkylating agents (cyclophosphamide, carmustine, etc.), nucleotide analogues (methotrexate, fluorouracil, etc.), antimetabolites (hydroxyurea, UFT, etc.), anti-tumor antibiotics (doxorubicin, mitomycin, etc.), topoisomerase I inhibitors (hydroxycamptothecin, topotecan, etc.), topoisomerase II inhibitors (etoposide, teniposide), antimitotic drugs (paclitaxel, vinorelbine, etc.), platinum derivatives (cisplatin, carboplatin, etc.), cytokine drugs (IL-2, IFNγ, etc.), monoclonal antibody (Her2 monoclonal antibody, PD-L1 monoclonal antibody, etc.) and so on, or these drugs may be administered in any order. It is satisfactory that the actual preferred method and administering sequence may vary in accordance with the above micellar tumor therapeutic vaccine agent, specific agents of alkylation agents, nucleotide analogues, antimetabolites, anti-tumor antibiotics, topoisomerase I inhibitors, topoisomerase II inhibitors, anti-mitotic drugs, platinum derivative drugs, cytokine drugs, monoclonal antibody drugs that are used, the particular type of tumor to be treated, and the particular subject to be treated.

The anti-cancer treatment of the present invention is suitable for the treatment of cancer of mammals including humans, such as cervix, mammary gland, ovary, prostate, lung, colon, kidney, stomach, pancreas, liver, head and neck, melanoma, leukemia and central nervous system; Particularly it is suitable for the treatment of cervical cancer and head and neck cancer.

The combined administration of the tumor-treating micellar polypeptide vaccine of the present invention and the at least another drug which is effective in cancer treatment, such as alkylation agents, nucleotide analogues, antimetabolites, anti-tumor antibiotics, topoisomerase I inhibitors, topoisomerase II inhibitors, anti-mitotic drugs, platinum derivative drugs, cytokine drugs, monoclonal antibody drugs, has a significant enhanced effect (synergy) without increasing its toxicity at the same time.

DETAILED DESCRIPTION OF EMBODIMENTS

Figure 1:
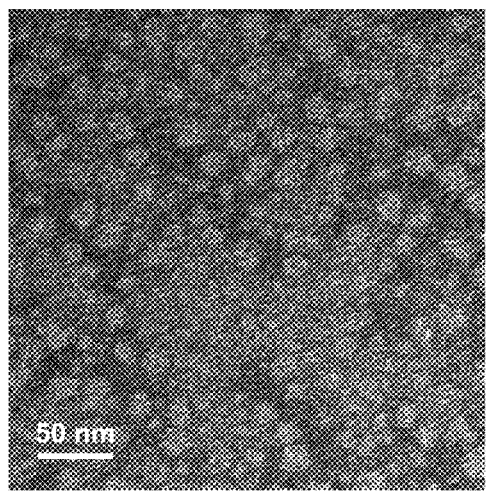
FIG. 1 is a transmission electron microscopy of micellar E7 vaccine.

Embodiment 1, Preparation of Micellar E7 Vaccine

E7 antigenic polypeptide is tumor-associated antigen which roots in human type-16 papilloma virus (HPV16), with palmitic acid molecule connected to the N-terminal, i.e., E7-20 polypeptide; $E7_{43-62}$ sequence: palmitic acid-GQAEPDRAHYNIVTFCCKCD;

Preparation of Stock Solution:

(1) 1 mL of absolute methanol is added into each tube that is separately prepared with 1 mg of E7-20 to prepare E7-20 stock solution with the concentration of 1 mg/mL.

(2) MPLA powder is dissolved in a mixed solution of 1:2 of methanol and chloroform to prepare MPLA stock solution with the concentration of 1 mg/mL.

(3) 30 mg of PEG-PE powder is weighed and added into 3 mL of chloroform to dissolve to prepare 10 mg/mL of PEG-PE stock solution.

1. Preparation of micelle vaccine solution. 10 mL of micelle vaccine is prepared according to the prescription of Table 1:

Step (1), 5 mL of PEG-PE stock solution is taken into a spin steaming bottle. 400 μL of MPLA stock solution and 1 mL of E7-20 stock solution are accurately measured and added into the spin steaming bottle, which is shaken lightly such that these two solutions are well mixed with the PEG-PE solution.

Step (2), under the condition of water bath heating, with the vacuum rotary evaporator, the organic solvent is removed (the rotational speed is 90 r/min, the water bath is at 40° C.). After the organic solvent is removed, PEG-PE, MPLA, and E7-20 form an evenly distributed membrane, which is put in a vacuum drier over night to completely remove the residual organic solvent and moisture.

Step (3), 10 mL of deionized water is added, the hydrated lipid membrane is incubated in the water bath at 53° C. for 30 minutes, such that micelle E7 vaccine solution with the uniform, colorless, and transparent appearance is obtained.

Step (4), after the solution stands still at room temperature for 2 hours, the solution is filtered and sterilized by a 0.22 μm filter membrane. Next, the solution is stored for future use under 4° C. (may be stored for at least two weeks).

TABLE 1

Micellar E7 Vaccine Prescription

| lipid/peptide (mol/mol) | lipid/MPLA (mass/mass) | PEG-PE solution concentration | MPLA solution concentration | E7-20 solution concentration |
|---|---|---|---|---|
| 44:1 | 79:1 | 5 mg/mL | 40 μg/mL | 100 μg/mL |

2. Preparation of micellar vaccine lyophilized powder. The prescription and Steps (1)-(3) are the same as above.

Step (4), the solution stands still at room temperature for 2 hours. Next, 0.5 g mannitol is accurately weighed and added into 10 mL of sample to be lyophilized. After the mannitol is dissolved completely, the solution is filtered by a 0.22 μm filter membrane. The solution is distributed into sterile ampoules in a way of 1 mL per ampoule, and is pre-frozen at −80° C. overnight.

Step (5), the sample is vacuum-lyophilized for 36 hours (with the vacuum degree of 0.1 mbar), such that a lyophilized agent is obtained.

Embodiment 2, Determination of Entrapment Efficiency of Lipid-Acidified E7/OT-1 Antigen Micelle Rhodamine-modified, fatty-acidified E7 antigenic polypeptide and OT-1 antigenic polypeptide (palmitic acid-EQLESIINFEKLTEWKD) is synthesized. Free fatty-acidified antigenic polypeptide cannot be dissolved in water and thus form suspensions, and fatty-acidified antigenic polypeptide, after being loaded by PEG-PE micelle, forms a stable solution. Thus, free antigenic polypeptide can be separated from the antigenic polypeptide loaded on micelle, and then the entrapment efficiency of antigenic polypeptide is calculated based on the change in the content of the antigenic polypeptide loaded on micelle in the solution. The entrapment efficiency=the amount of antigen to be entrapped/total antigen ×100%.

According to the proportions shown in Table 2 and Table 3, the micelles containing different proportions of polypeptides are prepared. The preparation process is carried out in the same manner as described in Embodiment 1. The prepared micelle vaccine solutions of different proportions are subjected to 14,000 g high-speed centrifugation for 30 minutes. The undissolved free antigenic polypeptide is separated from the antigen entrapped by micelle in the solution.

The maximal excitation wavelength of the rhodamine fluorescence labeled by the polypeptide is 535 nm and the maximum emission wavelength is 590 nm.

The antigen content in the solution is detected by fluorescence spectrophotometry, and then the effective entrapment efficiency of antigenic polypeptide is calculated according to the formula (see Table 2. Table 3, line 3). It can be seen that, in the condition where the mass ratio of PEG-PE to the fatty-acid-modified polypeptide is greater than or equal to 10:1, the entrapment efficiency is about 100%.

TABLE 2

Micellar Entrapment Efficiency at Different Mass Ratios of PEG-PE to E7 Antigenic Polypeptide

| lipid:peptide (w/w) | 50:1 | 20:1 | 10:1 | 5:1 | 2:1 | 1:1 |
|---|---|---|---|---|---|---|
| lipid:MPLA (w/w) | 100:1 | 100:1 | 100:1 | 100:1 | 100:1 | 100:1 |
| entrapment efficiency (%) | 100.00 | 100.00 | 100.00 | 97.99 | 67.76 | 25.48 |

TABLE 3

Micellar Entrapment Efficiency at Different Mass Ratios of PEG-PE to OT-1 Antigenic Polypeptide

| lipid:peptide (w/w) | 50:1 | 20:1 | 10:1 | 5:1 | 2:1 | 1:1 |
|---|---|---|---|---|---|---|
| lipid:MPLA (w/w) | 100:1 | 100:1 | 100:1 | 100:1 | 100:1 | 100:1 |
| entrapment efficiency (%) | 100.00 | 100.00 | 100.00 | 91.76 | 40.10 | 27.91 |

Embodiment 3, Physical Characterization of Micellar Polypeptide Vaccine

1. Morphological Observation of Micellar E7 Vaccine by Transmission Electron Microscope The micellar E7 vaccine solution prepared in Embodiment 1 is diluted with deionized water to dilute the concentration of PEG-PE to 0.1 mg/mL, and 10 μL of the sample solution is added dropwise to a copper mesh coated with carbon membrane which has been subjected to a glow discharge hydrophilization treatment. After 30-second absorption, the sample solution is absorbed by a filter paper. 10 μL of uranyl acetate (with the concentration of 2% (w/v)) is added dropwise for staining for 30 seconds. The staining solution is fully absorbed by a filter paper. The morphology of negatively stained micelle is observed with a transmission electron microscope (Tectai 20). The result is shown in FIG. 1 in which the micellar vaccines observed by a transmission electron microscope are homogeneous and spherical nanoparticles.

2. Particle Size Analysis of Dynamic Light Scattering of Micellar E7 Vaccine

Figure 2:
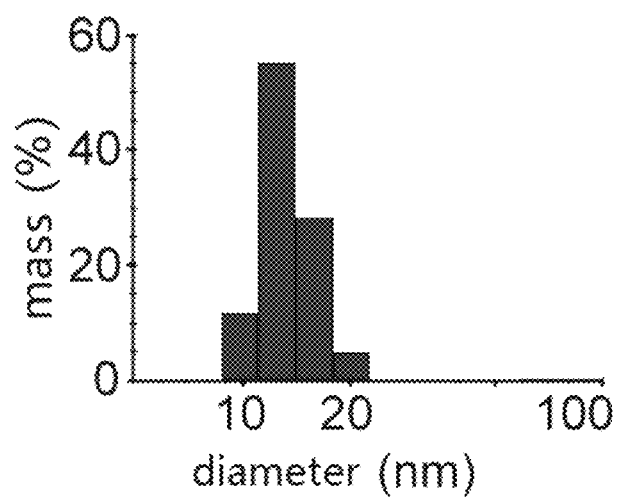
FIG. 2 is particle size analysis of dynamic light scattering of the micellar E7 vaccine.

The micellar E7 vaccine solution prepared in Embodiment 1 is diluted with deionized water to dilute the concentration of PEG-PE to 1 mg/mL. The sample is evenly mixed and stands still for 2 hours. 20 μL of sample is added into a quartz cuvette which has been washed by deionized water for more than 3 times without generating bubbles. The translucent part of the cuvette is wiped clean with a mirror paper. The cuvette is put into a sample pool of a dynamic light scatterometer (271-DPN) and pre-heated to set temperature of 25° C., and the time period of the set method is 10 seconds for each detection, and each group is detected 10 times. The results are shown in FIG. 2 in which the dynamic light scattering analysis shows that the particle size distribution of the micelles is between 10 and 20 nm.

Embodiment 4, Analysis of Subcutaneous Diffusion Behavior after Inoculation

1. Preparation of Sample:
(1) Preparation of Rhodamine E7 Solution

20 μL of 10 mg/mL DMSO stock solution of rhodamine-labeled, fatty-acidified E7 polypeptide (sequence: palmitic acid-GQAEPDRAHYNIVTFCCKCD, rhodamine labeled in amino acid K, synthesized in Jill Biochemical Co., Ltd.) is added to 1 mL of sterile water to obtain a fluorescent polypeptide solution with the concentration of 0.2 mg/mL.

(2) Preparation of Micellar Rhodamine E7 Solution 10 mg of PEG-PE powder is weighed and dissolved in 1 mL of chloroform in a test tube, and 0.2 mL of solution of rhodamine-labeled, fatty-acidified E7 polypeptide in methanol (1 mg/mL) is taken such that in micelle. The solution is gently shaken according to the method in Embodiment 1 to mix evenly. Nitrogen is used to blow and dry the solution to form a uniform thin membrane. The residual organic solvent and moisture are completely removed in a vacuum drier overnight. 1 mL of sterile normal saline is added, and 53° C. water bath incubation is conducted for 30 minutes for hydrated lipid membrane. A light purple uniform transparent solution is obtained, in which the concentration of fluorescent polypeptide is 0.2 mg/mL. After standing at room temperature for 2 hours and after filtration and sterilization through a 0.22 µm filter membrane, the solution is stored at 4° C. in reserve.

(3) Preparation of Lipidosome Rhodamine E7 Solution 7 mg of DPPC and 3 mg of cholesterol are dissolved in chloroform separately and then mixed in a test tube, and 0.2 mL of solution of rhodamine-labeled, fatty-acidified E7 polypeptide in methanol (1 mg/mL) is taken. The solution is blown with nitrogen to form an even thin membrane. The residual organic solvent and moisture are completely removed in a vacuum drier overnight. 1 mL of normal saline is added for hydration, and 53° C. water bath incubation is conducted for 30 minutes during which ultrasonic treatment is conducted for 1 minute. Next, extrusion is conducted with a Mini-Extruder (Avanti) extruder through a polycarbonate filter membrane with a pore size of 0.4 µm for at least 11 times. Finally, lipidosome with a particle size of about 400 nm is obtained. The concentration of fluorescence polypeptide is 0.2 mg/mL.

2. Experimental Grouping and Results 9 nude mice are divided into 3 groups each of which has 3 mice. 100 µL of samples of above agents are injected subcutaneously at the same position on the shoulder of the nude mice, respectively. 0 hour, 1 hours, 3 hours, 6 hours, 24 hours, 4 days, 6 days, 7 days after injection, the proliferation situation of fluorescent agents in mice is observed by vivo imaging.

Figure 3:
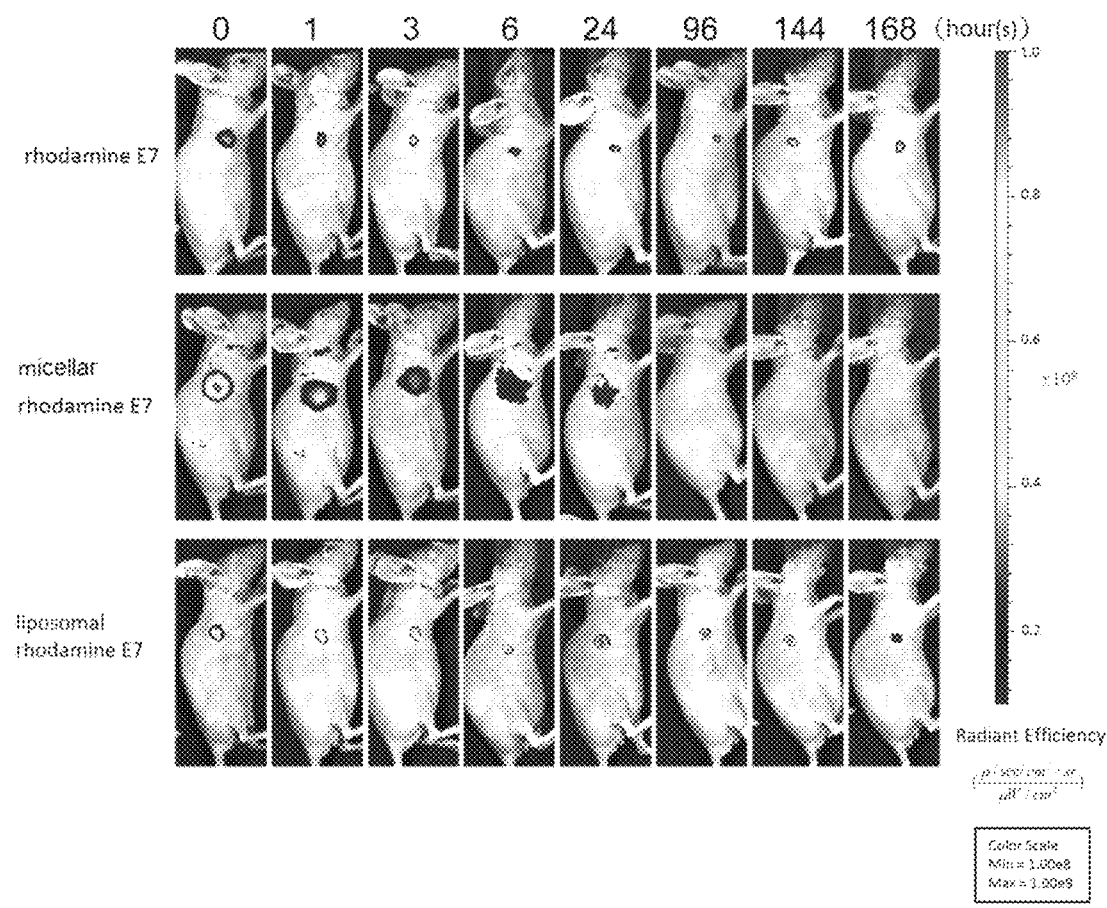
FIG. 3 shows that the micellar E7 vaccine can efficiently and rapidly spread subcutaneously, compared with lipidosome loaded E7 vaccine.

The results are shown in FIG. 3:

(1) Fatty-acidified E7 antigen is present in an aggregated form in aqueous solution, so that subcutaneous localized retention at the injection site is evident;

(2) Micellar antigenic polypeptide vaccine has a large subcutaneous diffusion speed and a large subcutaneous diffusion range;

(3) Compared with antigenic polypeptide vaccine, lipidosome antigenic polypeptide vaccine has a long subcutaneous localized retention time and is hard to diffuse.

In summary, micelle is more suitable agent form for subcutaneous administration.

Embodiment 5, Distribution of Draining Lymph Nodes

1. Preparation of Sample:

(1) Preparation of FITC-Labeled PEG-PE Micelle:

10 mg of PEG-PE powder is weighed and dissolved in 1 mL of in a test tube, and 0.6 mL of FITC-PEG-PE (FITC-labeled PEG-PE) chloroform stock solution is taken such that the molar ratio of FITC-PEG-PE molecules to total PEG-PE molecules in micelle is 5%. The solution is gently shaken according to the method in Embodiment 1 to mix evenly. Nitrogen is used to blow-dry the solution to form a uniform thin membrane. The residual organic solvent and moisture are completely removed in a vacuum drier overnight. 1 mL of normal saline is added, and 53° C. water bath incubation is conducted for 30 minutes for hydrated lipid membrane. A light yellow uniform transparent solution is obtained. After standing at room temperature for 2 hours and after filtration and sterilization through a 0.22 µm filter membrane, the solution is stored at 4° C. in reserve.

(2) Preparation of Rhodamine-Labeled Lipidosome:

7 mg of DPPC and 3 mg of cholesterol are dissolved in chloroform separately and then mixed in a test tube, and 50 µL of rhodamine-PE (rhodamine-labeled PE molecule) chloroform stock solution (2 mg/mL) is taken such that the molar ratio of Rho-PE to total lipidosome molecules is 1%. The solution is blown with nitrogen to form an even thin membrane. The residual organic solvent and moisture are completely removed in a vacuum drier overnight. 1 mL of normal saline is added for hydration, and 55° C. water bath incubation is conducted for 30 minutes during which ultrasonic treatment is conducted for 1 minute. Next, extrusion is conducted with a Mini-Extruder (Avanti) extruder through a polycarbonate filter membrane with a pore size of 0.4 µm, 0.1 µm for at least 11 times. Finally, single-chamber lipidosome with a particle size of about 100 nm is obtained.

2. Test Method 27 female C57BL/6 mice are divided into 3 groups each of which has 9 mice. 50 µL of FITC micellar vaccine and 50 µL of rhodamine lipidosome vaccine are injected subcutaneously at both sides of the shoulder, respectively. Normal saline is injected for blank control. 1, 2, and 3 days after injection, 3 mice are taken from each group and the axillary drainage lymph nodes on both sides are separated into a 1.5 mL EP tube. After cutting the lymph nodes into pieces with an ophthalmic straight shear, 200 µL of digestion solution (7.5 ml of RMPI1640 medium, 2% fetal bovine serum, 0.5 mg/ml collagenase IV, 40 U/ml deoxyribonuclease I, 10 nM HEPES) is added into each tube. After digestion at 37° C. for 30 minutes, 4 mL of complete medium is added into each tube for neutralization. After a 70 µm sieve and 500 g centrifugation for 5 minutes, cells are collected and re-suspended with FACS buffer to $5 \times 10^5$ cell/mL. The cell suspension is added to CD11c-APC antibody at 4° C. for incubation for 30 minutes according to the proportion in the Specification, and is washed with FACS buffer twice. Flow cytometry is used to analyze the proportion of fluorescent positive lymph node DC cells.

Figure 4A:
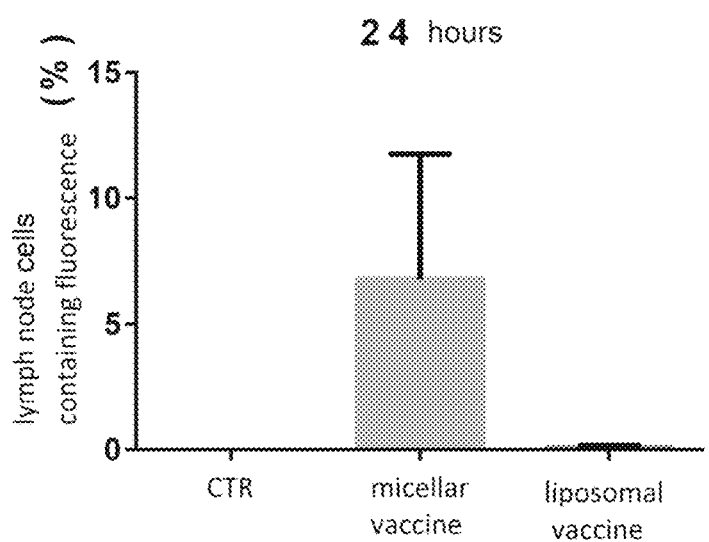
FIGS. 4A-4C show that the micellar vaccines can be efficiently swallowed by dendritic cells and macrophages in the lymph nodes.
Figure 4B:
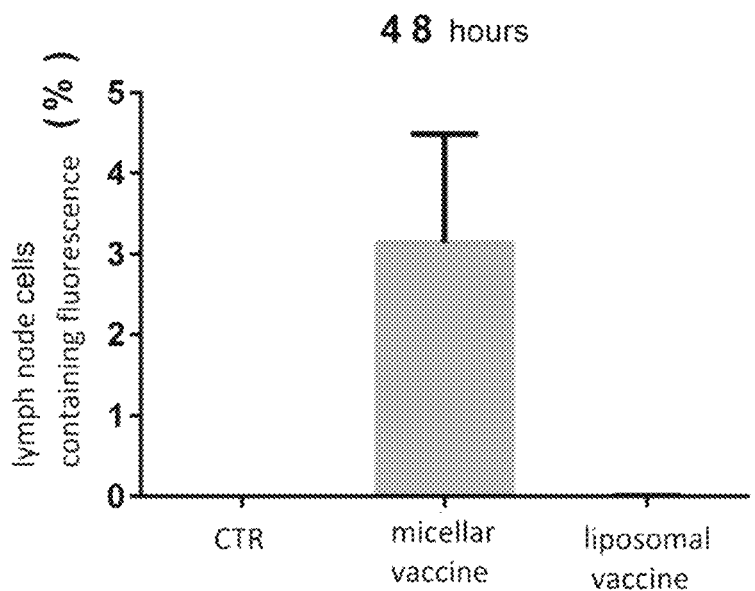
Figure 4C:
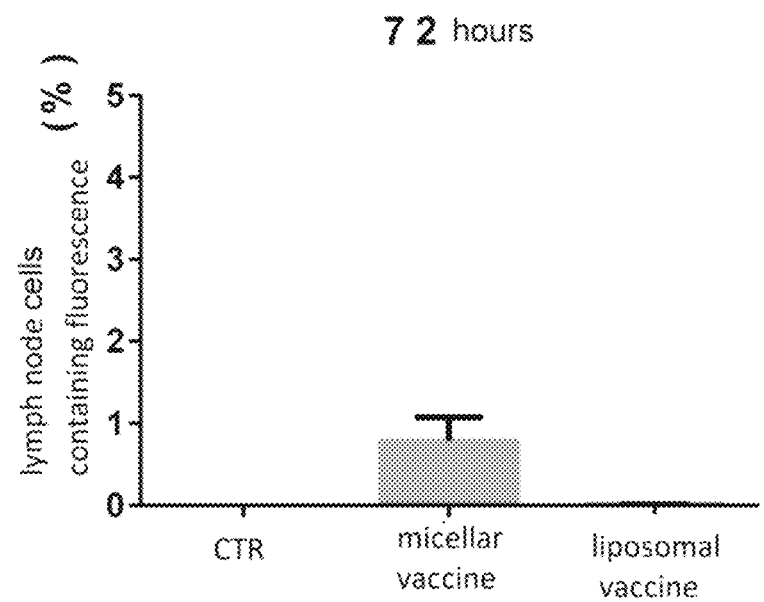

Result and conclusion: compared with lipidosome, micelles could be better phagocytosed by dendritic cells of lymph nodes. In addition, 2 days after inoculation, the proportion of dendritic cells in the lymph nodes that phagocytosing micelles is the highest, indicating that the micelles are more targeted relative to the dendritic cells of lymph nodes (FIGS. 4A-4C).

Embodiment 6, Experiment of MPLA Micellar Stimulating Macrophages In Vitro

Preparation of Sample:

(1) micellar E7 vaccine solution is prepared according to the method of Embodiment 1: 1 mL of PEG-PE stock solution is put into a test tube, and 100 µL of MPLA stock solution and 200 µL of E7-20 stock solution are accurately weighed and added into the test tube and are gently shaken to mix with the PEG-PE solution evenly. After the organic solvent is removed by blow-drying with nitrogen, PEG-PE, MPLA, and E7-20 form a uniform thin membrane. The residual organic solvent and moisture are completely removed in a vacuum drier overnight. 10 mL of normal saline is added, and 53° C. water bath incubation is conducted for 30 minutes for hydrated lipid membrane. An even, colorless and transparent solution is obtained, in which the concertation of MPLA is 100 μg/mL.

(2) micellar MPLA solution is prepared according to the method that is the same as that of (1): 10 mL of PEG-PE powder is dissolved in chloroform and mixed in a test tube. 100 μL of MPLA stock solution is added into the test tube. After being evenly mixed, the solution is blow-dried with nitrogen to form an even thin membrane. The residual organic solvent and moisture are completely removed in a vacuum drier ovenight. 4 mL of normal saline is added, and 53° C. water bath incubation is conducted for 30 minutes.

(3) comparison of MPLA with the same concentration as that of (1): 100 μL of MPLA stock solution is added into a test tube. The organic solution is blow-dried with nitrogen. The residual organic solvent and moisture are completely removed in a vacuum drier overnight. 1 mL of normal saline is added for hydration, and 53° C. water bath incubation is conducted for 30 minutes during which ultrasonic treatment is conducted for 5-10 minutes so as to prepare 100 μg/mL of MPLA suspension.

(4) preparation of MPLA lipidosome with membrane-hydration method and combined extrusion method, preparation method: 7 mg of DPPC and 3 mg of cholesterol are dissolved in chloroform separately and then mixed in a test tube, and 100 μL of MPLA stock solution is added to this test tube. After being evenly mixed, the solution is blown with nitrogen to form an even thin membrane. The residual organic solvent and moisture are completely removed in a vacuum drier overnight. 1 mL of normal saline is added for hydration, and 55° C. water bath incubation is conducted for 30 minutes during which ultrasonic treatment is conducted for 1 minute. Next, extrusion is conducted with a Mini-Extruder (Avanti) extruder through a polycarbonate filter membrane with a pore size of 0.4 μm 0.1 μm for at least 11 times. Finally, single-chamber lipidosome having a particle size of about 100 nm is obtained.

(5) unloaded lipidosome having lipid content as that of (4), preparation method: 7 mg of DPPC and 3 mg of cholesterol are dissolved in chloroform separately and then mixed in a test tube. The solution is blown with nitrogen to form an even thin membrane. The residual organic solvent and moisture are completely removed in a vacuum drier overnight. 1 mL of normal saline is added for hydration, and 55° C. water bath incubation is conducted for 30 minutes during which ultrasonic treatment is conducted for 1 minute. Next, extrusion is conducted with a Mini-Extruder (Avanti) extruder through a polycarbonate filter membrane with a pore size of 0.4 μm, 0.1 μm for at least 11 times. Finally, single-chamber lipidosome having a particle size of about 100 nm is obtained.

Mouse monocyte-macrophage cell line RAW264.7 (purchased from the Chinese Academy of Sciences cell bank) is cultured in DMEM medium containing 10% high-quality fetal bovine serum with 5% carbon dioxide at a temperature of 37° C. The cells are vaccinated in a 12-well plate with a cell count of $3\times10^5$/mL and 1 mL medium per well to be treated after adherent overnight.

Figure 5A:
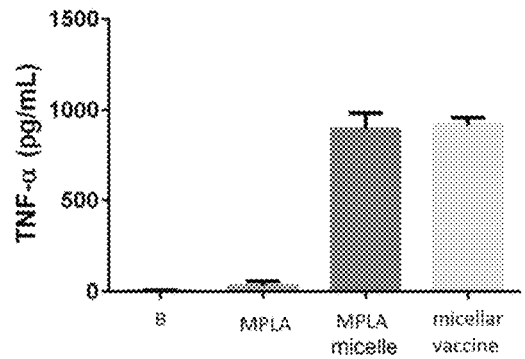
FIGS. 5A-5B show that the micellar vaccine can efficiently stimulate macrophages to secrete inflammatory cytokines, compared with lipidosome nanoparticles.

Processing method (1): Normal saline is used as blank control. MPLA, micellar vaccine, MPLA micelle are used as experimental groups. The acting final concentration of MPLA in each experimental group is 100 ng/mL. The amount of carrier or solvent in each control group is consistent with that of the corresponding experimental group. After 2-hour treatment for the cells, culture supernatant is collected and the concentration of extracellularly secreted cells TNF-α and other cytokines in the culture supernatant is detected by ELISA. The results are shown in FIG. 5A.

Figure 5B:
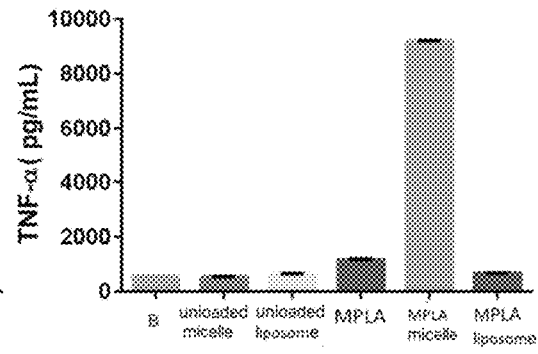

Processing method (2): Normal saline is used as blank control. Unloaded micelle and unloaded lipidosome are used as carrier comparing groups. MPLA, MPLA micelle, and MPLA lipidosome are used as experimental groups. The acting final concentration of MPLA in each experimental group is 100 ng/mL. The amount of carrier or solvent in each control group is consistent with that of the corresponding experimental group. After 3-hour treatment for the cells, culture supernatant is collected and the concentration of extracellularly secreted cells TNF-α and other cytokines in the culture supernatant is detected by ELISA. The results are shown in FIG. 5B.

Results and conclusion: MPLA is a ligand of TLR4 receptor, and the amount of secretion of proinflammatory cytokine TNF-α reflects the degree of activation of macrophages by MPLA. MPLA micelle and micellar vaccine have a considerable ability to activate cells (FIG. 5A). Compared with MPLA, the MPLA micelle and micellar vaccine can activate macrophages to a greater extent, whereas lipidosome cannot enhance the stimulating function of MPLA. Micellar MPLA enhances the efficiency of adjuvant of MPLA in activating macrophages (FIG. 5B).

Embodiment 7, Experiment of Micellar Polypeptide Vaccine Stimulating Dendritic Cell In Vitro Bone marrow-derived dendritic cells (BMDC) are obtained as follows: femoral and tibial bone marrow of a 6-8 weeks old female C57BL/6 mouse is taken in sterile PBS, the blown-over cell suspension is passed through a 70 μm sieve. Blood cells are dissociated and washed with PBS once or twice. The cells are seeded in a 100 mm (or 90 mm) culture dish and the cells are $2\times10^6$/10 mL/dish. The contents of medium are: RPMI-1640, 10% FBS, 100 U/mL of penicillin, 100 μg/ml of streptomycin, 2 mM of L-glutamine, 50 μM of β-mercaptoethanol, 200 U/mL of rmGM-CSF (recombinant mouse granulocyte macrophage colony stimulating factor). Culture conditions are 5% carbon dioxide and a temperature of 37° C. The medium is rehydrated 10 mL of liquid on day 3 and 10 mL of liquid is changed on day 6. After 8 days of induction, all the suspended cells are collected and identified by flow cytometry. CD11c (dendritic cell surface marker molecule) is considered as a DC cell marker, and the purity of DC cells is more than 90%.

PEG-PE unloaded micelle, MPLA suspension, MPLA micelle, and micellar vaccine solution are prepared according to the sample preparation method in Embodiment 6, wherein each concentration of MPLA is 100 μg/mL. Bone marrow-induced dendritic cells that have been cultured for 8 days are collected and seeded in a 24-well plate with a cell count of $5\times10^5$/mL and 1 mL medium per well. The prepared sample is treated after inoculation. Solvent saline is used as blank control group. Unloaded micelle is used as carrier control group. MPLA, MPLA micelle and micelle vaccine are used as experimental groups. The acting final concentration of MPLA in each experimental group is 100 ng/mL. The amount of carrier or solvent in each control group is consistent with that of the corresponding experimental group. After 24-hour treatment, culture supernatant and cells are collected. The concentration of extracellularly secreted cells TNF-α, IL-6 in the culture supernatant is detected by ELISA. Flow cytometry technique is used to analyze the expression of mature DC surface markers.

Figure 6A:
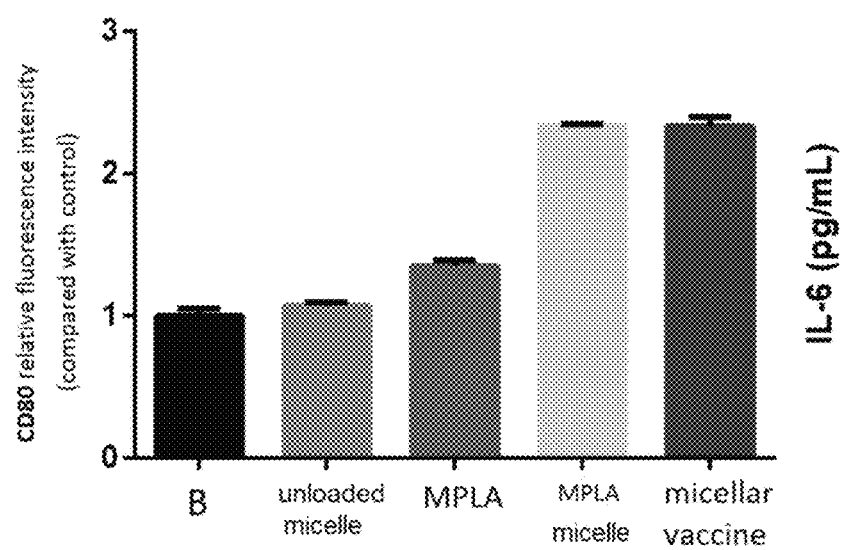
FIGS. 6A-6C show that the micellar vaccine can efficiently stimulate dendritic cells to be mature and activated.
Figure 6B:
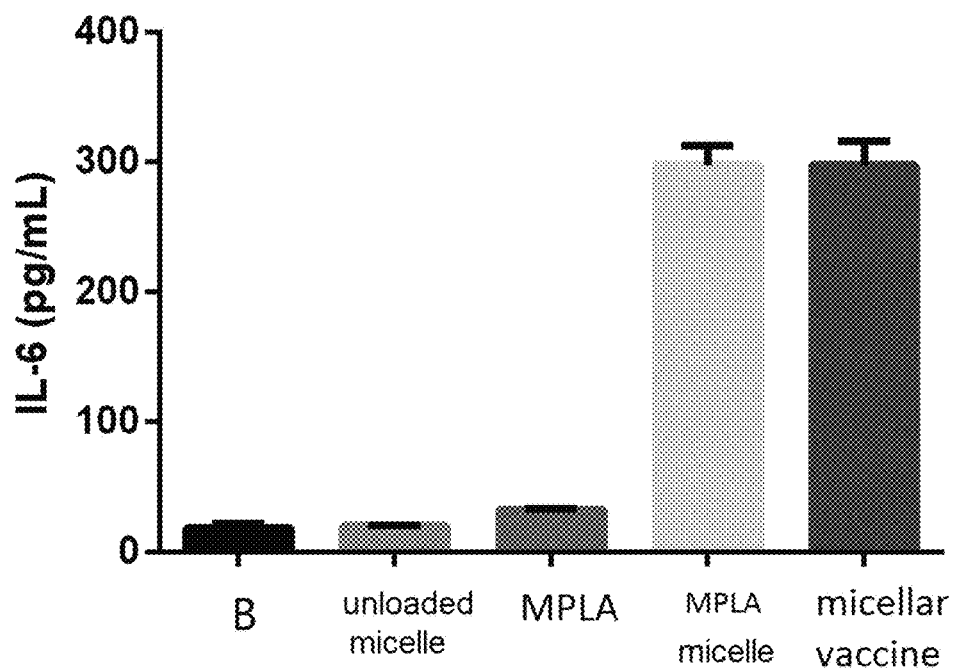
Figure 6C:
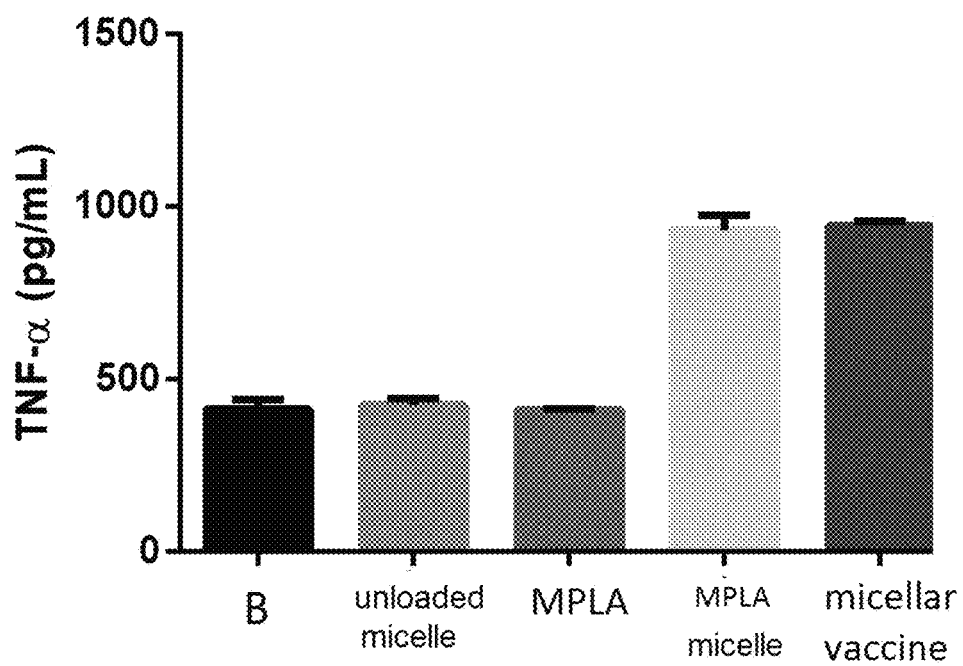

Result: dendritic cells are main effector cells of the vaccine in the body. The expression of dendritic cell surface CD80 (dendritic cell activation marker molecule) molecule and the secretion of cytokine TNF-α, IL-6 and so on reflect the activation of dendritic cells. Experiments show that micellar MPLA can activate dendritic cells more effectively than MPLA (FIGS. 6A-6C).

Embodiment 8, Experiment of Micellar E7 Vaccine Immune-Activating Cytotoxic T Cell (CTL)

Preparation of Sample:

(1) The micellar E7 vaccine solution is prepared according to the method of Embodiment 1. The concentration of PEG-PE is 2.5 mg/mL, the concentration of MPLA is 25 μg/mL and the concentration of E7-20 is 50 μg/mL.

(2) Preparation of mixed comparison group of MPLA without being loaded with carrier and E7-20. 100 μL of MPLA stock solution and 200 μL of E7-20 are evenly mixed in a test tube. The organic solution is blow-dried with nitrogen. The residual organic solvent and moisture are completely removed in a vacuum drier overnight. 4 mL of physiological saline is added, and 53° C. water bath incubation is conducted for hydrated lipid membrane for 30 minutes during which ultrasonic treatment is conducted for 5-10 minutes so as to prepare suspension with a MPLA concentration of 25 μg/mL and an E7-20 concentration of 50 μg/mL.

(3) preparation of lipidosome vaccine with membraneing-hydration method and combined extrusion method. Preparation method: 7 mg of DPPC and 3 mg of cholesterol are dissolved in chloroform separately and then mixed in a test tube.

100 μL of MPLA stock solution and 200 μL of E7-20 are added into the test tube. After being evenly mixed, the solution is blow-dried with nitrogen to form an even thin membrane. The residual organic solvent and moisture are completely removed in a vacuum drier overnight. 4 mL of physiological saline is added for hydration, and 55° C. water bath incubation is conducted for 30 minutes during which ultrasonic treatment is conducted for 3 minutes. Next, extrusion is conducted with a Mini-Extruder (Avanti) extruder through a polycarbonate filter membrane with a pore size of 0.4 μm, 0.1 μm for at least 11 times. Finally single-chamber lipidosome having a particle size of about 100 nm is obtained.

Said MPLA+E7-20 without carrier and in (2) and said lipidosome vaccine in (3) are used as control.

Female C57BL/6 mice are divided into 3 groups, each of which has 3 mice. Vaccination method is performed by subcutaneous multipoint injection of 100 μL per mouse. Normal saline solution is used as blank control group. For other experimental groups, the dosage of administration of MPLA is 125 μg/kg. The dosage of administration of E7 is 250 μg/kg. The dosage of administration of two agents that are micelle and lipidosome containing lipid is 12.5 mg/kg. 6 days later, mouse lymph nodes are separated, and pass a 70 μm screen. The fine count of lymph nodes is adjusted to $1 \times 10^7$/mL, 100 μL per well in a 96-well board with round bottom. 3 μg/mL of brefeldin A (BFA) and 5 μg/mL of $E7_{49-57}$ (amino acid sequence is RAHYNIVTF) are add. After the incubation is conducted for 6 hours in total, the cells are collected. The cell concentration is adjusted to $1 \times 10^6$. First, CD8 antibody is added and dyed for 20 minutes. Dyed cells are fixed by 4% paraformaldehyde under 4° C. for 30 minutes. After passing through 0.1% tritonX100 for 10 minutes, intracellular dyeing is conducted. IFNγ antibody is added and incubated for 20 minutes. The percentage of specifically activated IFNγ+CD8+T cells in lymph nodes CD8+T cells is analysied by the flow cell sorting technology.

Figure 7:
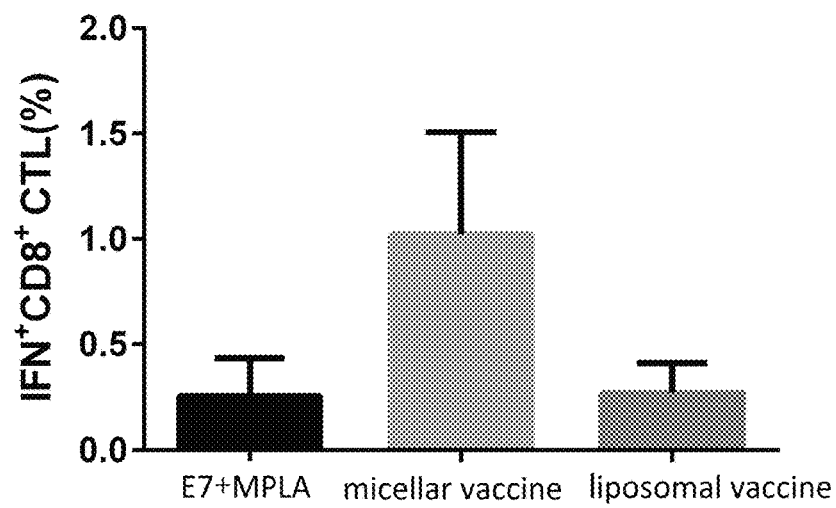
FIG. 7 shows that the micellar E7 vaccine can effectively produce CTL response to tumor-specific antigen.

Results: micellar polypeptide vaccine causes stronger specific CTL reaction than lipidosome vaccine (FIG. 7).

Embodiment 9, Experiment of Immunotherapy Effect Evaluation of Micellar Polypeptide Vaccine Preparation of Sample:

(1) 10 mL of micelle E7 vaccine solution is prepared according to the method of Embodiment 1, wherein the concentration of each ingredient is PEG-PE: 5 mg/mL, MPLA: 40 μg/mL, E7-20: 100 μg/Ml, respectively.

(2) The preparation of 10 mL of MPLA/PEG-PE micelle which has the same concentration as that of (1). 5 mL of PEG-PE stock solution is taken into a spin steaming bottle. 400 μL of MPLA stock solution is accurately weighed and added into the spin steaming bottle, which is lightly shaken such that the MPLA stock solution and PEG-PE solution are mixed well. In the vacuum rotary evaporator, the organic solvent (chloroform and methanol) is removed. The rotational speed is 90 r/min, and the water bath is 40° C. After the organic solvent is evacuated, PEG-PE and MPLA form evenly distributed membrane, which is put in the vacuum drier overnight, so as to completely remove residual organic solvent and moisture. 10 mL of normal saline is added. Hydrated lipid membrane is incubated in 53° C. water bath for 30 minutes, such that a solution with the uniform, colorless, and transparent appearance is obtained. After the solution stands still under the room temperature for 2 hours, the solution is filtered and sterilized by a 0.22 μm filter membrane. Next, the solution is stored for future use under 4° C.

(3) The preparation of 10 mL of E7/PEG-PE micelle which has the same concentration as that of (1). 5 mL of PEG-PE stock solution is taken into a spin steaming bottle. 1 mL of E7-20 stock solution is accurately weighed and added into spin steaming bottle, which is lightly shaken which is lightly shaken such that E7-20 stock solution and PEG-PE solution are mixed well. In the vacuum rotary evaporator, the organic solvent (chloroform and methanol) is removed. The rotational speed is 90 r/min, and the water bath is 40° C. After the organic solvent is evacuated, PEG-PE and E7-20 form evenly distributed membrane, which is put in the vacuum drier overnight, so as to completely remove residual organic solvent and moisture. 10 mL of normal saline is added. Hydrated lipid membrane is incubated in 53° C. water bath for 30 minutes, such that a solution with the uniform, colorless, and transparent appearance is obtained, after the solution stands still under the room temperature for 2 hours, the solution is filtered and sterilized by a 0.22 μm filter membrane. Next, the solution is stored for future use under 4° C.

30 female C57BL/6 mice are subcutaneously inoculated with TC-1 cells at the shoulder, $5 \times 10^4$ cells per mouse. On the 8th day after the tumor is inoculated, the mice are divided into four groups according to the average size of tumor, with 5 or 6 mice per group. On the 8th day, each group of vaccine is subcutaneously inoculated on the mouse on the far end of the same side where the tumor grows. The normal saline is used as blank control. The experimental groups are micelle vaccine, and two control groups MPLA/PEG-PE micelle and E7/PEG-PE micelle. The dose of subcutaneous immunization inoculation injection is 100

μL/mouse. The dosages of administration are PEG-PE: 25 mg/kg, MPLA: 200 μg/kg, E7-20: 500 μg/kg respectively. On the 11th, 15th, and 18th day, the inoculation is conducted once in the same way. From the 8th day to the 40th day, the tumor volume is monitored, and the survival time of mice is recorded.

Figure 8:
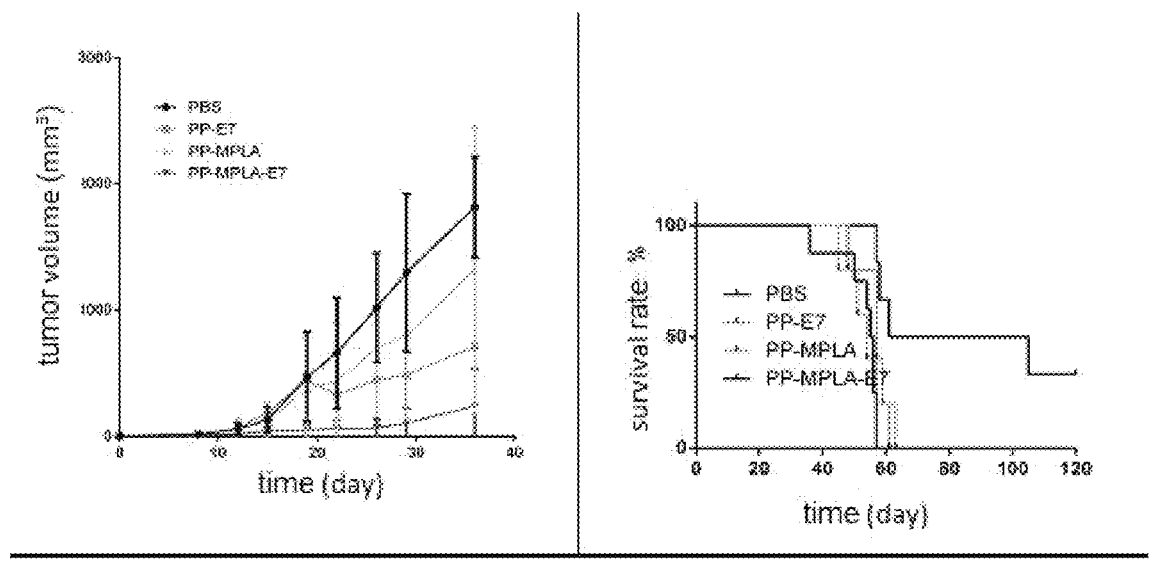
FIG. 8 shows that the micellar E7 vaccine can effectively reduce tumor growth rate and prolong the survival time of tumor-bearing mice.

Results: compared with blank control group, three treatment groups have certain inhibiting effects on the growing of tumor. The effect of micelle E7 vaccine group is the most significant. Two mice show that the tumor fades away. The record of survival time of mice shows that, there is no significant difference of survival time between MPLA/PEG-PE micelle group and E7/PEG-PE micelle group, two control groups and the blank control group. However, micelle E7 vaccine group can significantly extend the survival time of mice, and efficiently control the growing of tumor (FIG. 8).

Embodiment 10, Experiment of Evaluation of Prevention of Post-Operation Tumor Recurrence of Micellar Vaccine Preparation of Sample:
(1) 10 mL of micelle E7 vaccine solution is prepared according to the method of Embodiment 1, wherein the concentration of each ingredient is PEG-PE: 5 mg/mL, MPLA: 40 μg/mL, E7-20: 100 μg/mL, respectively.

(2) The preparation of 10 mL of MPLA/PEG-PE micelle which has the same concentration as that of (1):

5 mL of PEG-PE stock solution is taken into a spin steaming bottle. 400 μL of MPLA stock solution is accurately weighed and added into the spin steaming bottle, which is lightly shaken such that the MPLA stock solution and the PEG-PE solution are mixed well.

In the vacuum rotary evaporator, the organic solvent (chloroform and methanol) is removed. The rotational speed is 90 r/min, and the water bath is 40° C. After the organic solvent is evacuated, PEG-PE and MPLA form evenly distributed membrane, which is put in the vacuum drier overnight, so as to completely remove residual organic solvent and moisture.

10 mL normal saline is added. Hydrated lipid membrane is incubated in 53° C. water bath for 30 minutes, such that a solution with the uniform, colorless, and transparent appearance is obtained, after the solution stands still under the room temperature for 2 hours, the solution is filtered and sterilized by a 0.22 μm filter membrane. Next, the solution is stored for future use under 4° C.

(3) The preparation of 10 mL of E7/PEG-PE micelle which has the same concentration as that of (1) but does not contain MPLA:

5 mL of PEG-PE stock solution is taken into a spin steaming bottle. 1 mL of E7-20 stock solution is accurately weighed and added into the spin steaming bottle, which is lightly shaken such that E7-20 stock solution and PEG-PE solution are mixed well.

In the vacuum rotary evaporator, the organic solvent (chloroform and methanol) is removed. The rotational speed is 90 r/min, and the water bath is 40° C. After the organic solvent is evacuated, PEG-PE and E7-20 form evenly distributed membrane, which is put in the vacuum drier overnight, so as to completely remove residual organic solvent and moisture.

10 mL normal saline is added. Hydrated lipid membrane is incubated in 53° C. water bath for 30 minutes, such that a solution with the uniform, colorless, and transparent appearance is obtained. After the solution stands still under the room temperature for 2 hours, the solution is filtered and sterilized by a 0.22 μm filter membrane. Next, the solution is stored for future use under 4° C.

The animal experiment of evaluation of prevention of post-operation tumor recurrence experiment:

(1) 20 female C57BL/6 mice are divided into two groups. 50000 TC-1 tumor cells are subcutaneously inoculated in the shoulder.

(2) 21 days after the inoculation, when the size of tumor is 500 mm$^3$, the tumor excised by surgery. The wound is stitched. The local skin degerming treatment is conducted with iodophor.

(3) After the tumor is excised, the immunoprophylaxis group is subcutaneously inoculated 100 μL of micelle vaccine. The dosages of administration are PEG-PE: 25 mg/kg, MPLA: 200 μg/kg, E7-20: 500 μg/kg respectively. The other group is a blank control group using normal saline.

(4) On the seventh and the fourteenth day, a strengthened inoculation is conducted once. Records of the emergence of mice tumor are taken.

(5) On the 42nd day, two groups of mice that do not have reoccurrence of tumor are inoculated with $2 \times 10^5$ TC-1 tumor cells. Records of the emergence of mice tumor are taken.

Figure 9:
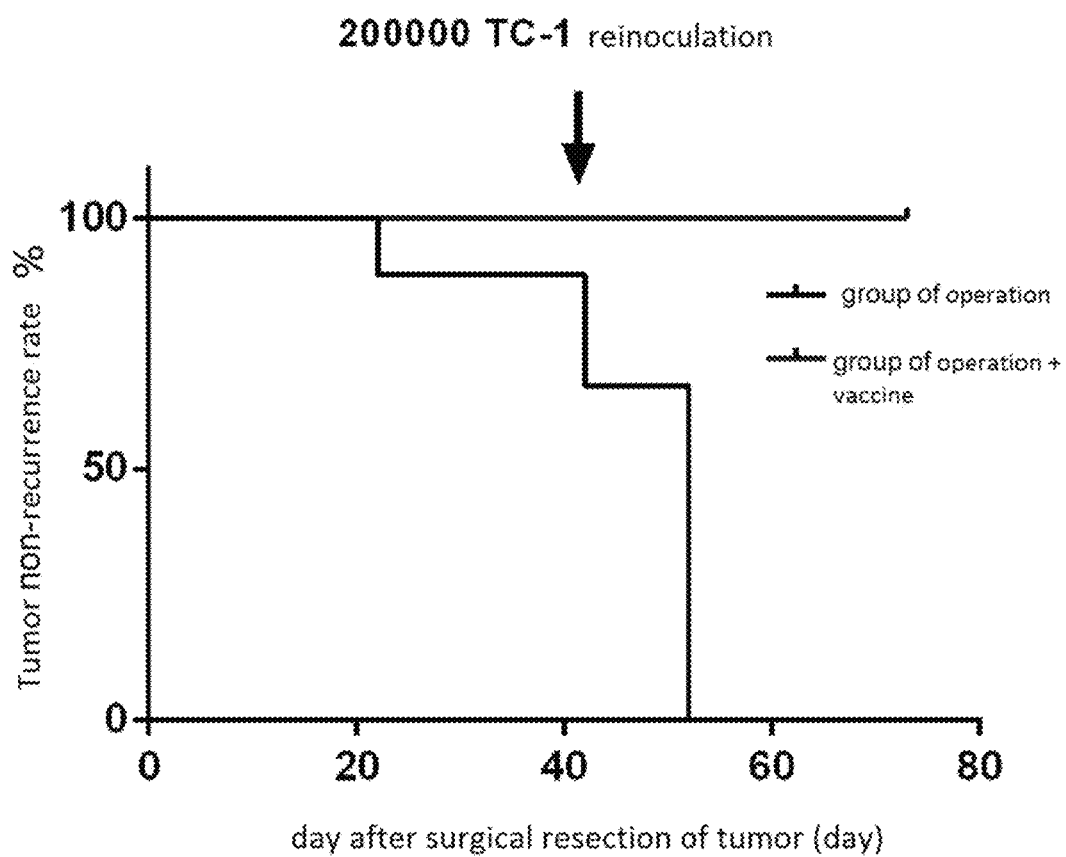
FIG. 9 shows that the micellar E7 vaccine can completely prevent tumor recurrence after tumor resection.
Figure 10:
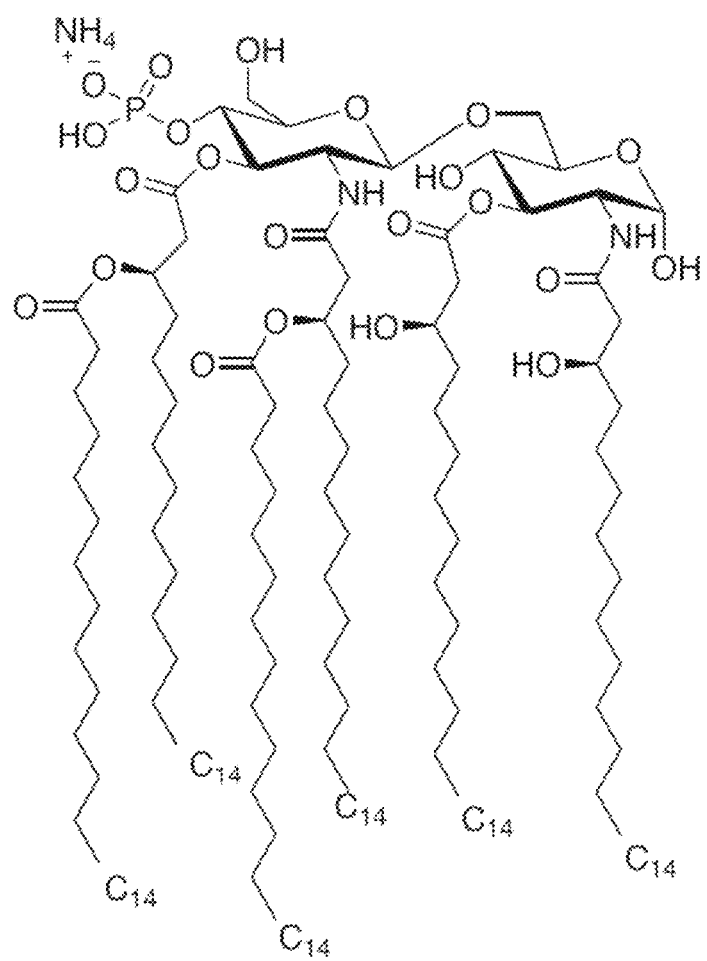
FIG. 10 shows the molecular structure of MPLA.

Results and conclusion: compared with blank control group, the inoculation of micelle vaccine have complete inhibiting effect on the reoccurrence of tumor after the tumor is excised by surgery. Results are shown in FIG. 9, the micelle vaccine can completely inhibit the reoccurrence of tumor after the tumor is excised by surgery. 42 days after the operation, under the circumstances that tumor cells are inoculated additionally, the medicine administration group can completely inhibit the growing of tumor 70 days after the operation.

Embodiment 11, Micellar Tumor Therapeutic Vaccine and Chemotherapeutics Medicine are Used in Combination to Treat Tumor Preparation of Sample:
10 mL of micelle E7 vaccine solution is prepared according to the method of Embodiment 1, wherein the concentration of each ingredient is PEG-PE: 5 mg/mL, MPLA: 40 μg/mL, E7-20: 100 μg/mL, respectively.

Figure 11A:
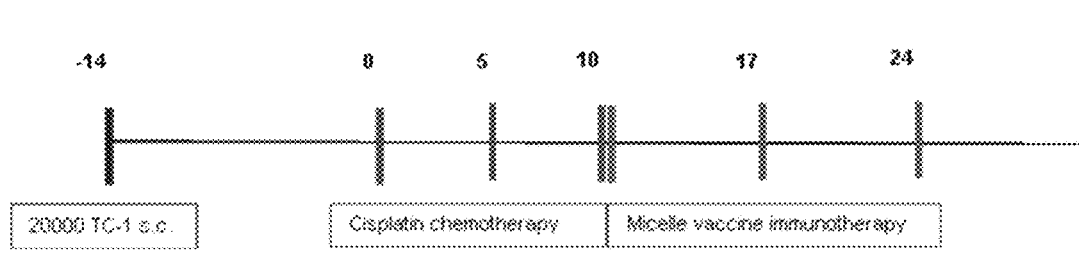
FIGS. 11A-11C show that using the micellar E7 vaccine in combination with chemotherapy to treat tumor significantly improves the tumor cure rate.

The animal experiment in which micellar tumor therapeutic vaccine and chemotherapeutics medicine are used in combination to treat tumor (the dosage regimen is shown in FIG. 11A):

(1) 30 female C57BL/6 mice are divided into two groups. 20000 TC-1 tumor cells are subcutaneously inoculated in the shoulder.

(2) 14 days after the inoculation, when the size of tumor is 100 mm$^3$, the mice are divided into groups, with 10 mice per group. There are two groups in total. In the two groups, the average sizes of tumors of mice are almost the same. The mice with tumors that are too big or too small are weeded out.

(3) Two groups of mice go through cis-platinum treatment for three times. For each time of treatment, cis-platinum solution is injected into caudal vein, with the injected dose of 5 mg/kg.

(4) After the third chemotherapeutics is finished, on the same day, the micellar tumor therapeutic vaccine combined treatment group of mice is subcutaneously inoculated 100 μL of tumor therapeutic micellar polypeptide vaccine. The dosage of administration is: E7-20 polypeptide dose in micelle E7 vaccine: 500 μg/kg. The other group is a blank control group using normal saline.

(5) On the seventh and the fourteenth day, a strengthened inoculation is conducted once. Records of the tumor volume and weight of mice are taken.

(6) 100 days after the last time of immunotherapy, in the combined treatment group, mice whose tumors has faded away are subcutaneously inoculated with $5 \times 10^5$ TC-1 tumor cells again. Records of the emergence of mice tumor are taken.

Figure 11B:
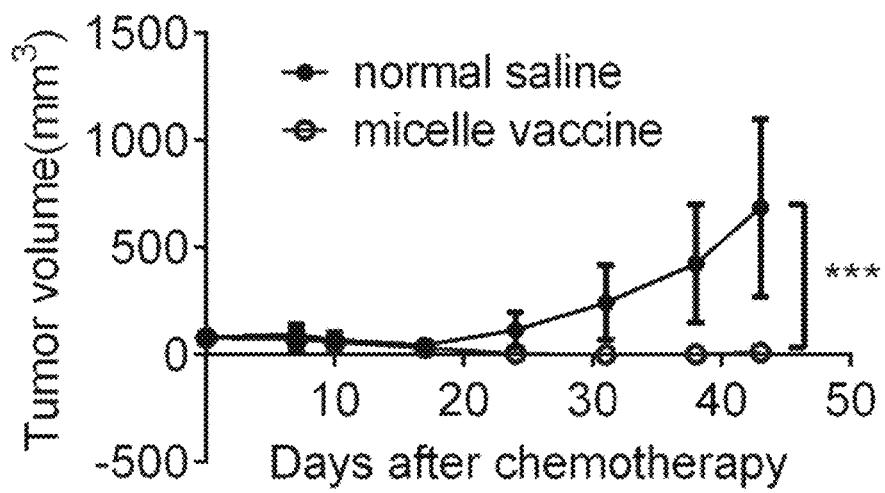
Figure 11C:
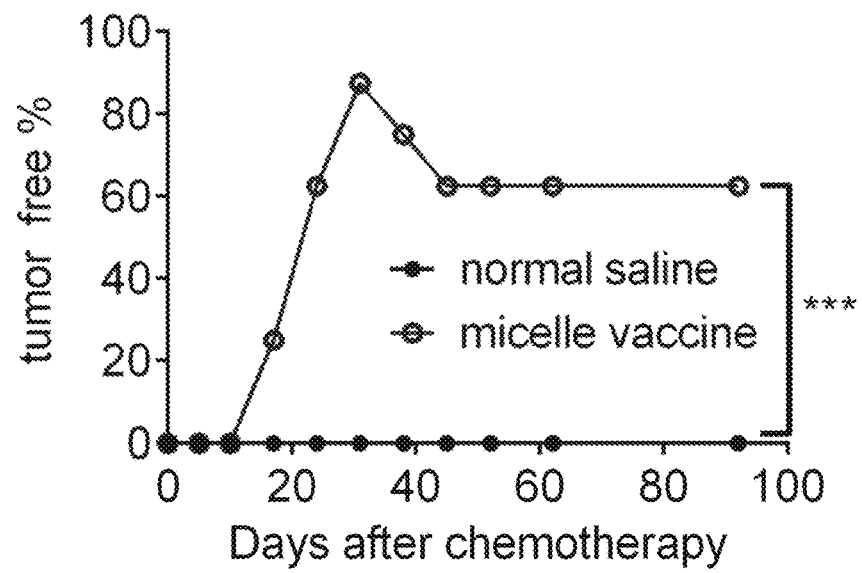

Results and conclusion: compared with pure chemotherapeutics control group, micellar tumor therapeutic vaccine, and chemotherapeutics medicine used in combination have more efficiently therapeutic effect on tumors (FIG. 11B). For more than 60% of the mice, tumors faded away completely (FIG. 11C). Moreover, 100 days after the treatment, under the circumstances that a large dose of tumor cells are continuously inoculated additionally, combined treatment group can completely inhibit the growing of tumor.

Embodiment 12, Micellar Tumor Therapeutic Vaccine and Therapeutic Antibody Used in Combination to Treat Tumor Preparation of Sample:
10 mL of tumor therapeutic micelle E7 vaccine solution is prepared according to the method of Embodiment 1, wherein the concentration of each ingredient is PEG-PE: 2.5 mg/mL, MPLA: 25 µg/mL, E7-20: 50 µg/mL respectively.

Control vaccine: no carrier loaded, MPLA: 25 µg/mL, E7-20: 50 µg/mL.

Figure 12A:
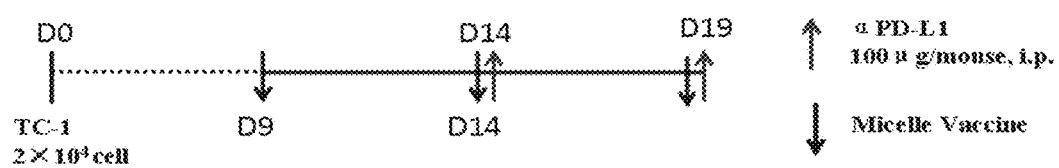
FIGS. 12A-12B and FIGS. 13A-13F show that using the micellar E7 vaccine in combination with therapeutic antibody PD-L1 to treat tumor significantly improves the therapeutic effect.

The animal experiment of micellar tumor therapeutic vaccine and chemotherapeutics medicine used in combination to treat tumor (the dosage regimen is shown in FIG. 12A):

(1) 80 female C57BL/6 mice are divided into two groups. 20000 TC-1 tumor cells are subcutaneously inoculated in the shoulder.

(2) 9 days later, the size of tumor is measured (about 50 mnm$^3$ in average). The mice are divided into 6 groups, with 10 mice per group. In the two groups, the average sizes of tumors of mice are almost the same. The mice with tumors that are too big or too small are weeded out.

(3) experimental groups are as below:
Control group without treatment: on the 0th, 5th, and 10th day after grouping, 100 µL of normal saline is subcutaneously injected.

Tumor therapeutic micellar polypeptide vaccine group: tumor therapeutic micellar polypeptide vaccine immune is conducted for 3 times. On the 0th, 5th, and 10th day after grouping, 100 µL is subcutaneously immunized respectively.

Tumor therapeutic micellar polypeptide vaccine and Control IgG homotype control antibody treatment combined control group: tumor therapeutic micellar polypeptide vaccine immunotherapy is conducted for three times. On the 0th, 5th, and 10th day after grouping, 100 µL is subcutaneously immunized respectively. Control IgG homotype control antibody treatment is conducted twice. On the 5th and 10th day, intraperitoneal injection is conducted respectively, 200 µg per mouse per time.

Antibody treatment group: αPD-L1 antibody treatment is conducted twice. On the 5th and 10th day intraperitoneal injection is conducted respectively, 200 µg per mouse per time.

Control vaccine and antibody treatment combined control group: MPLA/E7-20 immunotherapy is conducted for three times. On the 0th, 5th, and 10th day after grouping subcutaneously 100 µL is immunized respectively. αPD-L1 antibody treatment is conducted twice. On the 5th and 10th day, intraperitoneal injection is conducted respectively, 200 µg per mouse per time.

Tumor therapeutic micellar polypeptide vaccine and αPD-L1 antibody treatment combined treatment group: tumor therapeutic micellar polypeptide vaccine immunotherapy is conducted for three times. On the 0th, 5th, and 10th day after grouping, 100 µL is subcutaneously immunized respectively. αPD-L1 antibody treatment is conducted twice. On the 5th and 10th day intraperitoneal injection is conducted respectively, 200 µg per mouse per time. (This is no duplication, because the previous one is homotype control antibody.)

(4) Tumor volume and weight are measured twice each week, and the mouse survival rate is recorded.

Figure 12B:
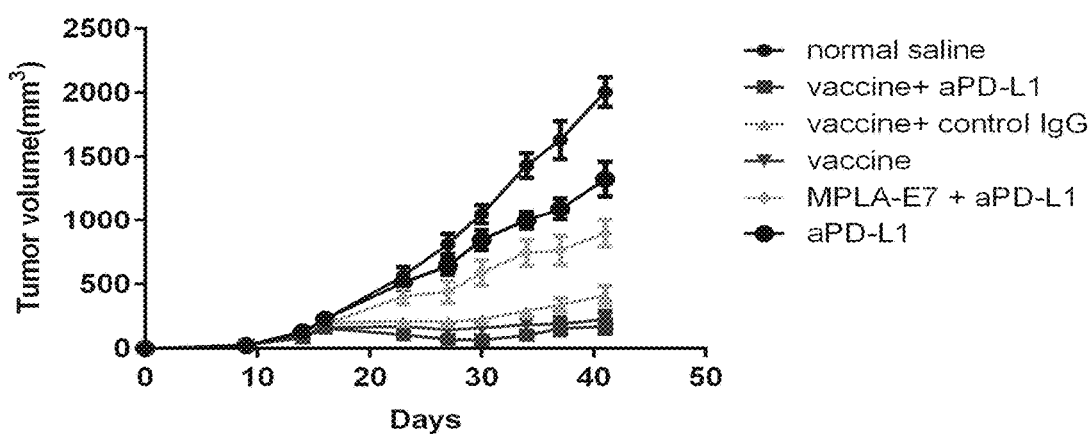
Figure 13A:
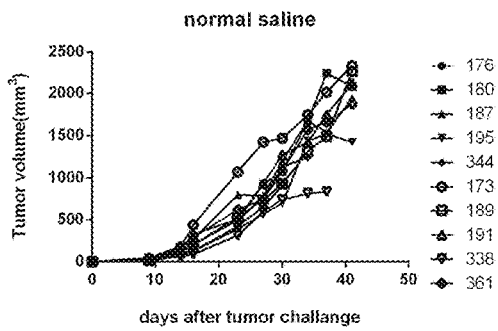
Figure 13B:
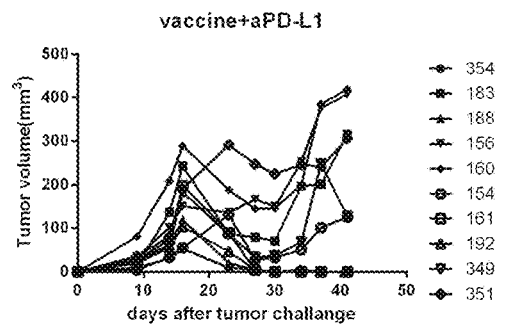
Figure 13C:
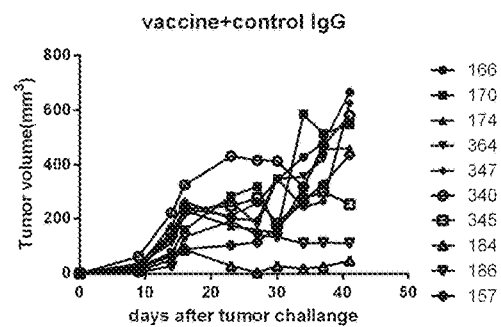
Figure 13D:
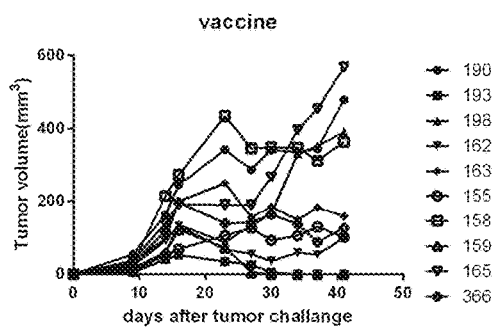
Figure 13E:
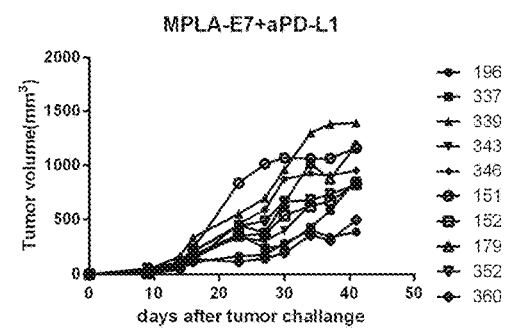
Figure 13F:
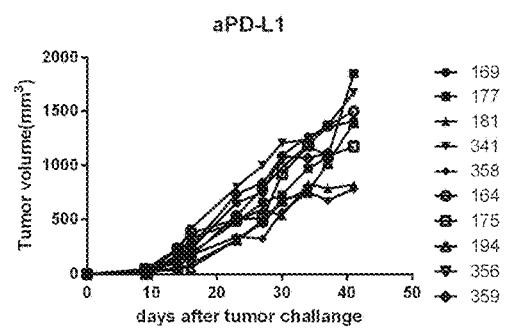

Results and conclusion: compared with pure micellar tumor therapeutic vaccine and control group, tumor therapeutic micellar polypeptide vaccine and treatment antibody used in combination have more efficiently therapeutic effect on tumor (FIG. 12B). For more than 40% of the mice, tumors faded away completely. Correspondingly, in the treatment group which uses tumor therapeutic micellar polypeptide vaccine, for 20% of the mice, tumors faded away completely. In contrast, in the treatment group which solely uses αPD-L1 antibody, no mouse has the tumor faded away (FIGS. 13A-13F).

Finally, it should be noted that the above embodiments are merely used to help a person with ordinary skill in the art to understand the nature of the present invention, and should not be interpreted as the limitation of the scope of the present invention.

What is claimed:

1. A method for preparing a micellar polypeptide vaccine formed by self-assembling pegylated phospholipid (PEG-PE), antigenic polypeptide, and immunoadjuvant, comprising:

step (1): dissolving PEG-PE carrier molecules, antigenic polypeptide molecules, immunoadjuvant molecules in volatile organic solvent or water or phosphate buffer solution to prepare carrier molecule solution, antigenic polypeptide solution, and immunoadjuvant solution;

step (2): evenly mixing the carrier molecule solution, the antigenic polypeptide solution, and the immunoadjuvant solution obtained in step (1) according to the proportion of each component in the micellar polypeptide vaccine to obtain a mixed solution;

step (3): removing all organic solutions from the mixed solution obtained in step (2) to make the carrier molecules, the antigenic polypeptide molecules and the immunoadjuvant molecules form a mixed lipid membrane that is evenly distributed;

step (4): dissolving the mixed lipid membrane obtained in step (3) in normal saline, hydrating the lipid membrane evenly in an incubating condition, and then standing the lipid membrane at room temperature for a certain time to obtain micellar vaccine solution; and step (5): sterilizing the micellar vaccine solution obtained in step (4); wherein a molar ratio of the pegylated phospholipid to the antigenic polypeptide to the immunoadjuvant is 720: 4-160: 3-80; and the immunoadjuvant is monophosphoryl lipid A (MPLA); wherein the volatile organic solvent in the step (1) is methanol, chloroform, dichloromethane, ethyl acetate, ethyl alcohol, acetone, glacial acetic acid, or a mixture of two or more selected from the group consisting of the methanol, the chloroform, the dichloromethane, the ethyl acetate, the ethyl alcohol, the acetone, and the glacial acetic acid;

removing the organic solutions in the step (3) is achieved with a vacuum rotary evaporator, under a condition of water bath heating; and the incubating condition in the step (4) includes incubating with water bath at 40-60° C. for 20-60 minutes.

2. The method of claim 1, further comprising:

step (6): adding a certain amount of lyophilizing protective agent to the micellar vaccine solution, and then lyophilizing the micellar vaccine solution to prepare lyophilized micellar vaccine powder; wherein the lyophilized protective agent is mannitol, lactose, sorbitol, or dextran, the concentration of the lyophilized protective agent is 0.05 g/ml.

* * * * *